(12) United States Patent
Gokaraju et al.

(10) Patent No.: US 10,206,964 B2
(45) Date of Patent: *Feb. 19, 2019

(54) **SYNERGISTIC ANTI-INFLAMMATORY COMPOSITIONS COMPRISING *BOSWELLIA SERRATA* EXTRACT**

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Venkata Kanaka Ranga Raju Gokaraju, Vijayawada (IN); Trimurtulu Golakoti, Vijayawada (IN); Kiran Bhupathiraju, Vijayawada (IN); Venkata Krishna Raju Alluri, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 229 days.

This patent is subject to a terminal disclaimer.

(21) Appl. No.: 14/735,360

(22) Filed: Jun. 10, 2015

(65) Prior Publication Data

US 2015/0290270 A1 Oct. 15, 2015

Related U.S. Application Data (63) Continuation of application No. 13/062,066, filed as application No. PCT/IN2009/000505 on Sep. 14, 2009, now Pat. No. 9,101,599.

(30) Foreign Application Priority Data

Sep. 15, 2008 (IN) .......................... 2229/CHE/2008

(51) Int. Cl.
A61K 36/324 (2006.01)

(52) U.S. Cl.
CPC .................................. A61K 36/324 (2013.01)

(58) Field of Classification Search
None
See application file for complete search history.

(56) References Cited

U.S. PATENT DOCUMENTS

| | | | |
|---|---|---|---|
| 4,499,076 A | 2/1985 | Ohashi et al. | |
| 5,629,351 A * | 5/1997 | Taneja | C07J 63/008 514/765 |
| 5,720,975 A | 2/1998 | Etzel et al. | |
| 2003/0199581 A1 * | 10/2003 | Seligson | A61K 31/19 514/548 |
| 2004/0073060 A1 * | 4/2004 | Gokaraju | C07J 63/008 562/498 |
| 2004/0166182 A1 | 8/2004 | Zhang | |
| 2006/0246115 A1 | 11/2006 | Rueda et al. | |

FOREIGN PATENT DOCUMENTS

| | | |
|---|---|---|
| JP | 59-13726 | 1/1984 |
| JP | 6-9479 | 1/1994 |

OTHER PUBLICATIONS

Ernst, "Indian Frankincense" from "Complimentary therapies for pain management" (2007) 5 pages.
Rose, et al., "Frankincense Profile a Scent from the Bible", Internet Archive date: Apr. 8, 2004 [Retrieved from the Internet on: Jul. 9, 2016] Retrieved from: <URL: https://web/archive.org/web/20050408221352/http://www.aromaticplantproject.com/articles_archive/frankincense_profile.html>.
Che, et al., "Herb-Herb Combination for Therapeutic Enhancement and Advancement: Theory, Practice and Future Perspectives", Molecules 2013, 18, 5125-5141.
Song, et al., "A chemical family-based strategy for uncovering hidden bioactive molecules and multicomponent interactions in herbal medicines", Scientific Reports, Dec. 7, 2015, www.nature.com/scientificreports.
Y, et al., "Effect of hexane extract of Boswellia serrata oleo-gum resin on chemically induced liver damage", Pak J Pharm Sci., Apr. 2006;19(2): 129-33.
Author Abu Bakr Mohammad.Bin Zakariyya Al-Razi, Title of publication—Kitaab-al-Ilaawi-fil-Tibb, vol. VII, Page(s) being submitted—4 (p. 4-7) ( Ref. pg. no. of publication:35 ), Publication Date—1958 AD, Publisher—Dayerah-al-Ma'aarif Usmania, Place of Publication—Hyderabad, India.
Author Mohammad Najmul Ghani Khan, Title of publication—Khazaain-al-Advia, vol. VIII, Page(s) being submitted—5 (p. 8-12) ( Ref. p. No. of publication:410 411 ), Publication Date—1926 AD, Publisher—Nadeem Yunus Printer / Sheikh Mohd Basheer & Sons, Place of Publication—Lahore, India.
Author Title of publication—Rasatantrasarah Evam Siddhaprayogasamgrahah, Page(s) being submitted—4 (p. 13-16) ( Ref.p. No.of publication:318 ), Publication Date—1990, Publisher—Krishan Gopal Ayurveda Bhawan, Place of Publication—Ajmer, India.

* cited by examiner

*Primary Examiner* — Amy L Clark
(74) *Attorney, Agent, or Firm* — Kramer Amado, P.C.

(57) ABSTRACT

The present invention discloses synergistic nutraceutical or pharmaceutical or dietary supplement anti-inflammatory compositions comprising therapeutically effective combination of an extract selectively enriched in 3-O-acetyl-1 1-keto-β-boswellic acid (AKBA) derived from *Boswellia serrata* and *Boswellia serrata* non-acidic resin extract (BNRE). The composition(s) can be used to prevent, control and treat inflammation and several inflammatory related diseases including asthma, osteoarthritis, rheumatoid arthritis, endothelial dysfunction and the like. The invention further discloses the amelioration of pro-inflammatory biomarker proteins or molecules, whose expression/production is altered during inflammatory diseases.

14 Claims, 7 Drawing Sheets

FIG. 1

Fig. 2A. Chromatogram at 252 nm.

Fig. 2B. Chromatogram at 210 nm.

SYNERGISTIC ANTI-INFLAMMATORY COMPOSITIONS COMPRISING *BOSWELLIA SERRATA* EXTRACT

CROSS-REFERENCE TO RELATED APPLICATIONS

This application is a continuation of parent U.S. application Ser. No. 13/062,066, filed on. Mar. 3, 2011, which is a national stage application based on International Application No. PCT/IN2009/000505, published as WO 2010/029578. The disclosure of each prior application is incorporated by reference herein in its entirety.

FIELD OF INVENTION

The present invention provides synergistic nutraceutical, pharmaceutical and dietary supplement compositions comprising *Boswellia serrata* extract selectively enriched in 3-O-acetyl-11-keto-β-boswellic acid (AKBA) and *Boswellia serrata* non-acidic resin extract (BNRE). The composition(s) can be used to prevent, control and treat inflammation and disease conditions related to or associated with inflammation including asthma, arthritis, endothelial dysfunction and the like.

The invention further includes the amelioration of pro-inflammatory biomarker proteins or molecules, whose expression/production is altered during inflammatory diseases.

BACK GROUND OF THE INVENTION

The gum resin of the plant *Boswellia serrata* (Burseraceae) has long been in use for the treatment of rheumatoid arthritis and gout by the practitioners of Ayurvedic medicines in the Indian system of medicine. Various extracts of the gum resin have shown potent anti-inflammatory and anti-atherogenic activity in laboratory animals [Cuaz-Pérolin et al., *Arterioscler Thromb Vasc Biol* February 2008]. Incensole acetate a *Boswellia* compound isolated was proved to be a NFκB inhibitor and useful as anti-inflammatory compound. [Moussaieff et al., *Mol Pharmacol* 72, 1657-1664, 2007]. It was observed in the past that the ethanolic extract of the gum resin of *B. serrata* inhibits the formation of Leukotriene B4 in rat peritoneal neutrophils. Leukotriene B4 is one of the important mediators of inflammatory reactions [Ammon, H. P. T. et al., Planta Medica, 57, 203 (1991)]. The extract of *Boswellia* was found to be a potent anti-arthritic agent [Kimmatkar et al; *Phytomedicine.* 2003 January; 10(1):3-7.], and immunomodulatory agent [Pungle et al; *Indian J Exp Biol.* 2003 December; 41(12): 1460-1462]. The cholesterol lowering action of *Boswellia serrata* was also proved. [Zutshi U et al, Indian J Pharmac. 18, 182-183, 1986.]. In fact, a randomized, double blind, placebo controlled, crossover clinical trial with *Boswellia* extract on a group of patients with osteoarthritis of knee exhibited statistically significant mean improvements with respect to reduction in pain, decreased swelling and increased knee flexion [Kimmatkar N, et. al., *Phytomedicine* 2003; 10: 3-7]. In an open non-randomized equivalence study, 30 patients with chronic colitis were administered either *Boswellia* gum (300 mg thrice daily) or sulfasalazine (1 g thrice a day) and the therapeutic effects shown by *Boswellia* were comparable to those exhibited by sulfasalazine [Gupta I, et. al., Planta Med. 2001; 67: 391-395]. In another equivalency study, *Boswellia* standardized extract exhibited therapeutic improvements, comparable to, or better than, mesalazine in a randomized, double-blind study on patients with active Crohn's disease [Gerhardt H, et. al., Z Gastroenterol 2001; 39: 11-17]. *Boswellia* gum resin also showed statistically significant improvement in patients with bronchial asthma in a six-week double-blind, placebo controlled study [Gupta I, et. al., Eur J Med Res 1998; 3: 511-51].

The patents also describe various activities of *Boswellia*. Some are quoted below:

PCT Patent publication WO03074063A1 and granted Indian patent #205269 relates to a process for producing a fraction enriched up to 100% of 3-O-acetyl-11-keto-β-boswellic acid. An organic solvent extract of gum resin from *Boswellia* species is first subjected to oxidation and then acetylation or vice versa. This converts the less potent boswellic acids present in the fraction to AKBA. This treated fraction is subjected to further purification and separation by chromatographic separation techniques to enhance its purity and to remove contaminants there from. This process provides an access to a fraction enriched in 10-100% AKBA for therapeutic applications.

The European patent publication EP1637153A1 relates to the association of *Boswellia Serrata* extract with plant antifibrotic agent as medicament particularly against inflammatory and fibrotic courses. In such association *Boswellia Serrata* is present as dry extract in quantity from 5 to 50% and the plant antifibrotic agent as dry extract in quantity from 50 to 95% by weight.

The U.S. Pat. No. 5,629,351 relates to a novel fraction comprising a mixture of boswellic acids, wherein the fraction exhibits anti-inflammatory and antiulcerogenic activities. Also disclosed is a novel boswellic acid compound exhibiting anti-inflammatory, antiarthritic and antiulcerogenic activities. Also disclosed is a process for isolating a boswellic acid fraction and individual boswellic acids therefrom.

The U.S. Pat. No. 5,720,975 relates to the use of incense (olibanum), incense extracts, substances contained in incense, their physiologically acceptable salts, their derivatives and their physiological salts, pure boswellic acid, of physiologically acceptable salts, of a derivative, of a salt of the derivative, for production of a medicament for the prevention or treatment of Alzheimer's disease.

The U.S. Pat. No. 5,888,514 refers to a composition for treating a mammal having a condition characterized by bone or joint inflammation where extract of *Boswellia serrata* is used as one of the ingredients.

The PCT patent publication WO08036932A2 relates to compositions and methods, for making compositions derived from *Boswellia* species (frankincense or olibanum) having uniquely elevated volatile oil, boswellic acids, and polysaccharide compounds, particularly, human oral delivery formulations, and methods for use of such compositions, useful e.g. for treating/preventing arthritis, inflammatory disorders, osteoarthritis, rheumatoid diseases and low back pain.

There is however no prior art, to the best of inventors knowledge, relating to the compositions comprising *Boswellia* extract especially AKBA enriched extract along with *Boswellia serrata* non-acidic resin extract (BNRE) for the prevention, control and treatment of inflammatory conditions.

SUMMARY OF THE INVENTION

The main object of the present invention is to provide synergistic nutraceutical or pharmaceutical or dietary supplement compositions comprising therapeutically effective combination of *Boswellia serrata* extract or fraction selectively enriched in 3-O-acetyl-11-keto-β-boswellic acid (AKBA) and *Boswellia serrata* non-acidic resin extract (BNRE) for the prevention, control or treatment of inflammation and/or disease conditions associated with or related to inflammation including asthma, atherosclerosis, endothelial dysfunction, osteoarthritis, rheumatoid arthritis and the like.

In yet another aspect, the invention provides synergistic compositions comprising enriched AKBA extract and *Boswellia serrata* non-acidic resin extract for the prevention, control and treatment of one or more components of inflammation and associated or related diseases including but not limited to asthma, atherosclerosis, endothelial dysfunction, osteoarthritis, rheumatoid arthritis, allergic rhinitis, dermatitis, psoriasis, cystic fibrosis, inflammatory bowel diseases, multiple sclerosis, diabetes, cognition, neurological disorders, collagen synthesis, anti-aging, metabolic disorders, systemic lupus erythematosis, uveitis, post-angioplasty restenosis, glomerulonephritis, gastrointestinal allergies, nephritis, conjunctivitis, chronic obstructive pulmonary disease, occupational asthma, eczema, bronchitis, hay fever, hives, allergic disorders and for conditions like wheezing, dyspnea, non productive cough, chest tightness, neck muscle tightness, rapid heart rate, chest pain, joint pain and several other conditions associated thereof in mammals.

In still yet another aspect, the invention provides synergistic compositions comprising AKBA enriched *Boswellia serrata* extract and *Boswellia serrata* non-acidic resin extract (BNRE) for the prevention, control and treatment of one or more components of other inflammatory diseases including arthritis or rheumatoid arthritis. Nonlimiting EXAMPLEs of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, joint disorders, spondyloarthropaties (ankylosing spondylitis), osteoarthritis, hyperuricemia and arthritis associated with acute gout, chronic gout and systemic lupus erythematosus and degenerative arthritis.

The further objective of the present invention is to provide synergistic compositions for the amelioration of the expression and/or production of biomolecules or biomarkers associated with inflammation and/or disease conditions associated with inflammation, osteoarthritis, rheumatoid arthritis, cartilage degradation, which include but limited to 5-lipoxygenase (5-LOX), 5-Lipoxygenase activating protein (FLAP), macrophage/adipocyte fatty acid-binding protein-2 (aP2/FABP), interferon-gamma (IFN-γ), interleukin-4 (IL-4), intercellular cell adhesion molecule (ICAM)-1, vascular cell adhesion molecule (VCAM)-1, Matrix metalloproteinase (MMP)-3, TNF-α and IL-1β in mammals.

DETAILED DESCRIPTION OF THE INVENTION

Inflammation is a response of the vascular tissues to stimuli such as pathogens, damaged cells or allergic agents which enter into the body. It is a protective mechanism by the organism to remove harmful pathogens or agents and protect the tissues. Pro-inflammatory cytokines such as TNFα, IL-1β, IL-6, GM-CSF and CD4+, Th2 subset derived IL-4, IL-5 and IL-13 lymphokines are considered as the key factors of immunopathogenesis of inflammatory diseases [Knight D A, et. al., *J. Allergy Clin. Immunol.* 2001; 108: 797-803]. 5-Lipoxygenase is an enzyme critical for leukotriene synthesis from arachidonic acid, a key step in the inflammatory process. Leukotrienes are key mediators of inflammatory disease.

The activation and gene expression of 5-lipoxygenase (5-LOX) is responsible for the disease condition. The 5-Lipoxygenase activating protein (FLAP) is an 18 kDa integral membrane protein which activates 5-Lipoxygenase by specifically binding arachidonic acid and transferring it to the enzyme [Mancini et. al., 1993]. FLAP is therefore responsible for the production of leukotrienes. Hence blocking or down regulating the 5-LOX and FLAP is a novel therapeutic approach for the treatment and control of inflammatory condition.

Atherosclerosis is also an inflammatory disease characterized by the formation of arterial lesions over a period of several decades at sites of endothelial cell dysfunction. Inflammation plays important role at many stages of atherosclerotic plaque development. [K K Berg et al., Scandinavian Journal of Immunology, 69, 36-42].

Matrix Metalloproteinases (MMPs) are zinc dependent endopeptidases, that are capable of breaking down all kinds of extra cellular matrix proteins, such as collagen, that are normally found in the spaces between cells in tissues. MMPs are divided primarily into three principal groups, the fibroblast collagenase-1 (MMP-1) formed of the collagenases, the gelatinases comprising gelatinase A (MMP-2) and the gelatinase B (MMP-9), and the stromelysines comprising stromelysine-1 (MMP-3) and matrilysine (MMP-7). An excess of metalloproteinase leads to degradation of biomolecules such as collagen, proteoglycon and gelatin, which can have fatal consequences on epidermis and can also generate diseases of the cartilages, inflammation etc.

Boswellia serrata Extract Selectively Enriched in AKBA (BE30%):

Boswellia resin and extracts have been in use for the treatment of inflammatory diseases for ages. Boswellic acids were identified as the active compounds responsible for the beneficial effects attributed to Boswellia serrata. The minor compound 3-O-acetyl-11-keto-β-boswellic acid (AKBA) was identified as the most potent 5-lipoxygenase inhibitor of all the boswellic acids [Sailer E R et. al., British J Pharmacology. 1996, 117(4): 615-8]. As such the extracts or fractions enriched in the AKBA content presumed to show better efficacy compared to the natural extracts. The inventors, in their PCT application # PCT/IN05/000074, dated 7 Mar. 2005 and PCT Patent publication WO03074063A1 and granted Indian patent 205269, have demonstrated a process for producing Boswellia serrata extract selectively enriched in 30-100% AKBA from commercial Boswellia serrata extracts, which contain around 85% total boswellic acids by titrimetric method of analysis and around 3% AKBA (BE3%) by HPLC method of analysis. The said enriched Boswellia extract is a unique composition characterized by the lack of significant quantities of the triterpene components commonly present in regular Boswellia serrata extracts, except AKBA, which is a minor component (up to 3%) in regular Boswellia extracts, but it is a major component in the enriched extract. The components present in the regular Boswellia extracts are 1) (3-boswellic acid, 2) 3-O-acetyl-β-boswellic acid, 3) 11-keto-β-boswellic acid, 4) 3-O-acetyl-11-keto-β-boswellic acid, 5) 9-ene-β-boswellic acid, 6) 3α-hydroxyurs-9,11-diene-24-oic acid, 7) 2α,3α-hydroxyurs-12-ene-24-oic acid. The major components of unique Boswellia serrata extract enriched in AKBA used in the present inventive composition are 1) 3-O-acetyl-β-boswellic acid, 2) 3-O-acetyl-9(11)-dehydro-β-boswellic acid, 3) 3-O-acetyl-11-keto-β-amirin, 4) 3-O-acetyl-11-keto-α-boswellic acid.

The said Boswellia serrata extract containing 30% AKBA (BE30%) was tested in several in vitro assays and it was found to be superior to commercial Boswellia serrata extract containing 3% AKBA (BE3%) [Roy S. Kanna, et. al., DNA and Cell Biology, 2005, 24(4): 244-255]. In direct comparison experiments, the said enriched Boswellia serrata extract (BE30%) also showed significantly higher inhibition against adjuvant-induced inflammatory response, in Wistar Albino rats, compared to a natural Boswellia extract containing 3% AKBA [Roy S, et al., Antioxidants & Redox Signaling, 8, 3 & 4, 2006]. Boswellia serrata extract selectively enriched to 30% AKBA (BE30%) is used to demonstrate the present invention.

Boswellia serrata Non-acidic Resin Extract (BNRE):

The Boswellia serrata resin contains acidic compounds, non-acidic compounds and sugars. During the execution of commercial process for regular Boswellia serrata extract (85% total boswellic acids, BE3%), the acidic fraction, which contains predominantly triterpene acids including boswellic acids, is separated from the rest of resin components. The sugars and other polymeric materials also got separated into the aqueous phase during the enrichment of total boswellic acids. The remaining water immiscible non-acidic low polar compounds are separated as Boswellia oil fraction/extract. These non-acidic or neutral low polar compounds are either absent or present at very low concentration both in commercial Boswellia extracts and AKBA enriched Boswellia extracts. The presence of these non-acidic components becomes even lower with the increasing enrichment of AKBA.

The said non-acidic Boswellia oil has been a significant component of Boswellia serrata gum resin. However, it has very limited commercial utility and it is mostly discarded as a waste material. Potential utilization of this fraction has been long overdue. The inventors have found an unexpectedly utility for Boswellia serrata oil for making synergistic compostions. Boswellia serrata non-acidic resin extract (BNRE), a fraction obtained after removing the volatile compounds from the Boswellia serrata oil, has been used in the present invention. Boswellia serrata non-acidic resin extract (BNRE) has been obtained in the following manner, a) the Boswellia serrata gum resin was dispersed in methyl isobutyl ketone (MIBK) solvent and the insoluble gum materials were separated by filtration, b) the MIBK solution was extracted repeatedly with 2% KOH solution to remove the acidic compounds, c) the MIBK layer was then washed successively with water and brine, d) the MIBK layer was evaporated under reduced pressure at 60-70° C. and the volatile components are then removed from the oily residue under vacuum at 75-85° C. to obtain a viscous oil, which is herein after referred as Boswellia serrata non-acidic resin extract or BNRE. Alternatively, the BNRE can also be prepared by a) preparing the alcohol extract of Boswellia serrata resin followed by, b) partitioning the alcohol extract between an aqueous alkali solution and a water immiscible organic solvent, c) separation of the organic solvent layer, followed by evaporation of the solvent to obtain non-acidic Boswellia oil extract, d) removal of volatile compounds at high temperature and vacuum to obtain Boswellia serrata non-acidic resin extract (BNRE).

Figure 1:
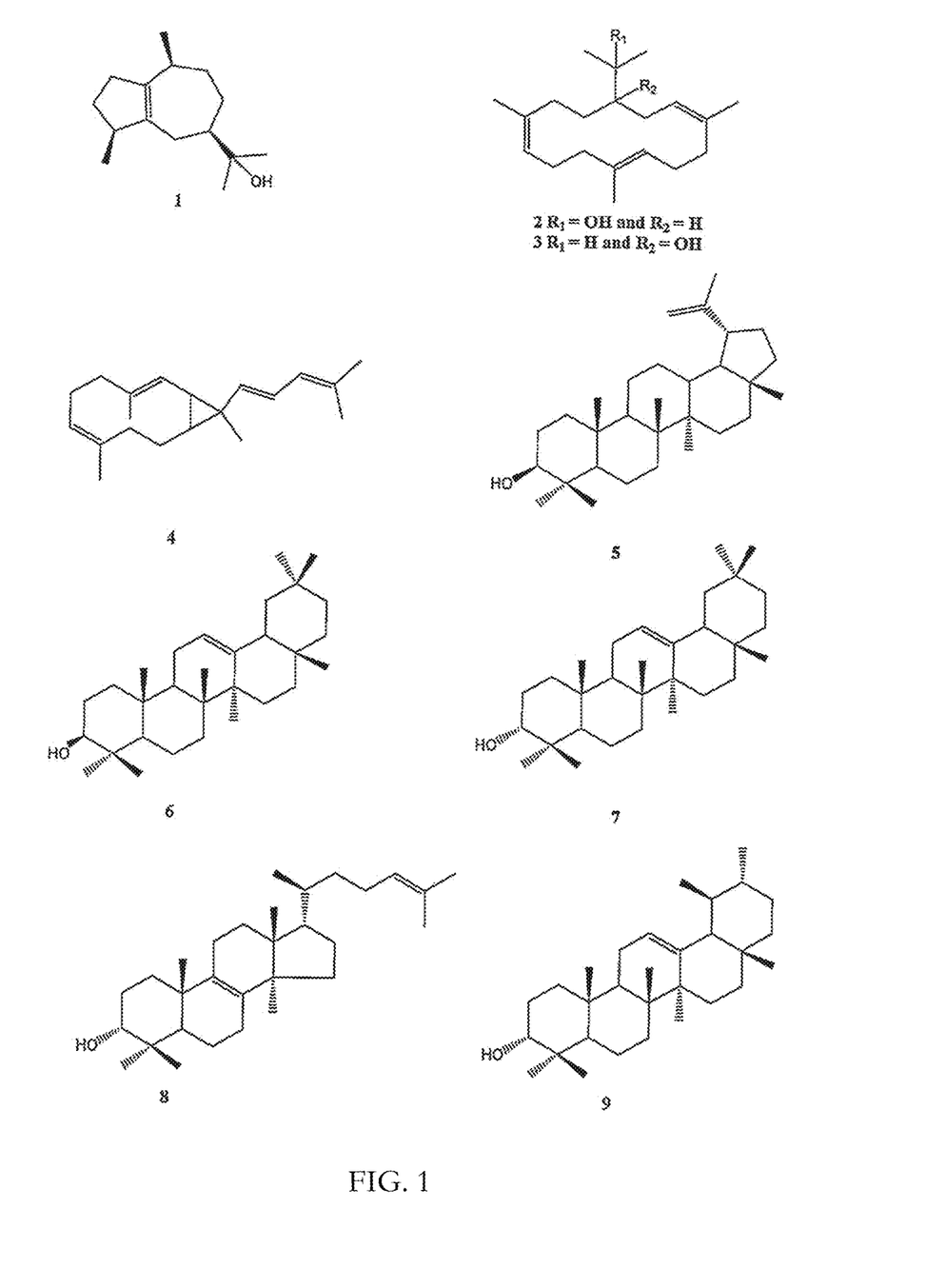
FIG. 1 shows structural formulae 1-9 representing prominent compounds of *Boswellia serrata* non-acidic resin extract (BNRE).
Figure 2A:
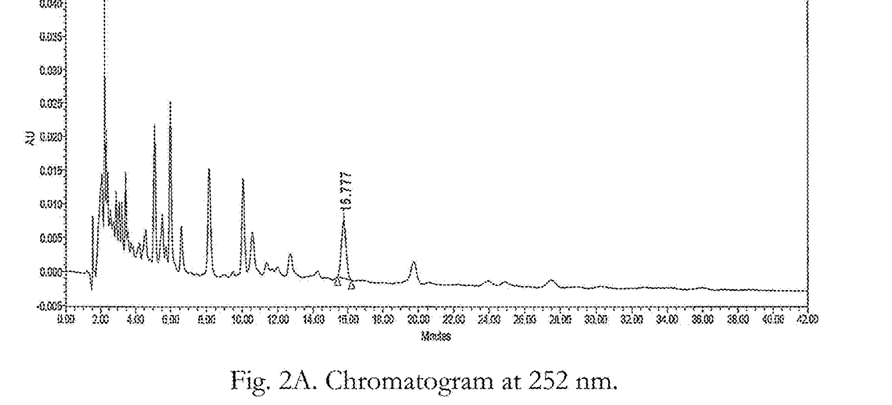
FIGS. 2A and 2B show the HPLC chromatogram depicting the phytochemical profile of the *Boswellia serrata* non-acidic resin extract (BNRE) at 252 nm (FIG. 2A) and at 210 nm (FIG. 2B).
Figure 2B:
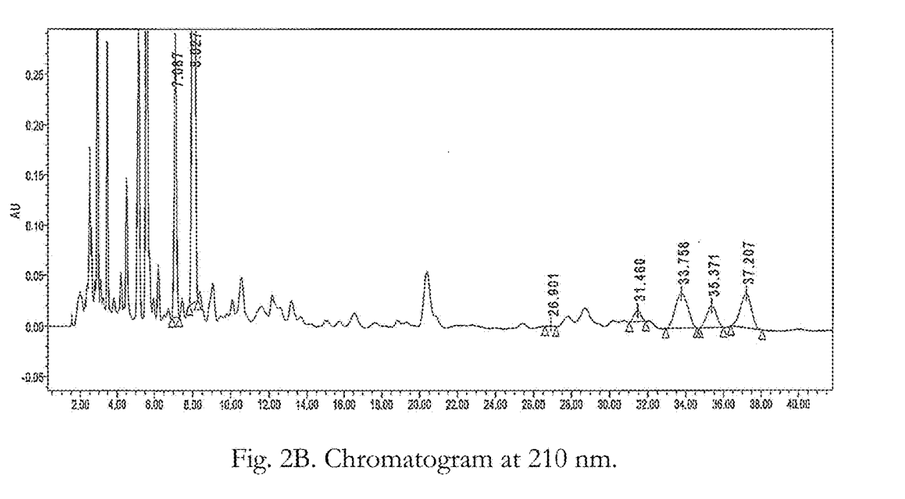

The above Boswellia serrata non-acidic resin extract (BNRE) was unexpectedly found to have a unique composition. The inventors have carried out extensive separation of BNRE using repeated column chromatography and high performance liquid chromatography and isolated several diterpenoid and triterpenoid compounds. The structures of the compounds were rigorously characterized using $^1$H NMR, $^{13}$C NMR, DEPT, HSQC and HMBC, Mass spectral data. The compounds identified are guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9) as depicted in FIG. 1. The pure compounds so obtained were used as phytochemical markers to standardize the Boswellia serrata non-acidic resin extract (BNRE). The results of the phytochemical analysis are summarized in the Table 1 and the chromatogram depicting the phytochemical profile of BNRE is presented in FIGS. 2A and 2B.

Figure 3A:
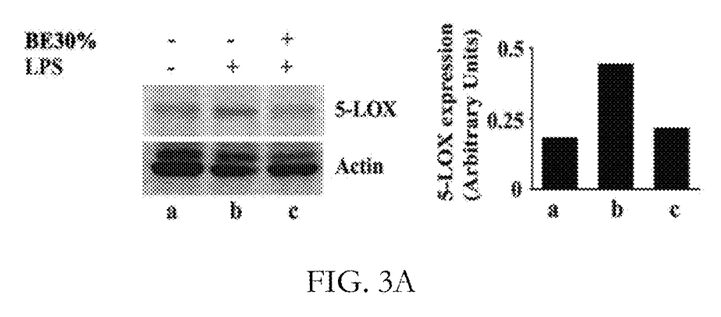
FIGS. 3A and 3B depict representative immuno blots showing BE30%-induced inhibition of 5-Lipoxygenase (FIG. 3A) and FLAP (FIG. 3B) expressions in human monocytes THP-1 cells. In each respective panel, bar diagram represent the normalized densitometric values (in arbitrary units). The bars a, b and c represent control, LPS treated and LPS+BE30% treated cells respectively.
Figure 3B:
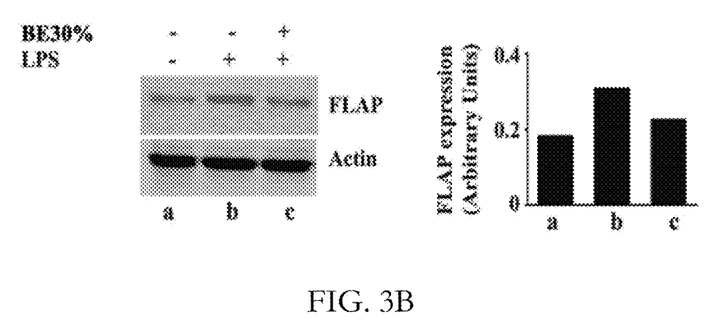

Synergistic Compositions Comprising *Boswellia* Extracts:

The inventors have conducted several cell based in vitro anti-inflammatory studies on broad array of *Boswellia* extracts and *Boswellia serrata* extracts selectively enriched in AKBA. These studies have shown unexpectedly that the *Boswellia serrata* extract selectively enriched in 30% 3-O-acetyl-11-keto-β-boswellic acid (AKBA)[BE30%] potently down-regulated the LPS induced expression of 5-LOX and FLAP in THP-1 human-monocyte-macrophage cells in vitro (FIGS. 3A and 3B).

Figure 4:
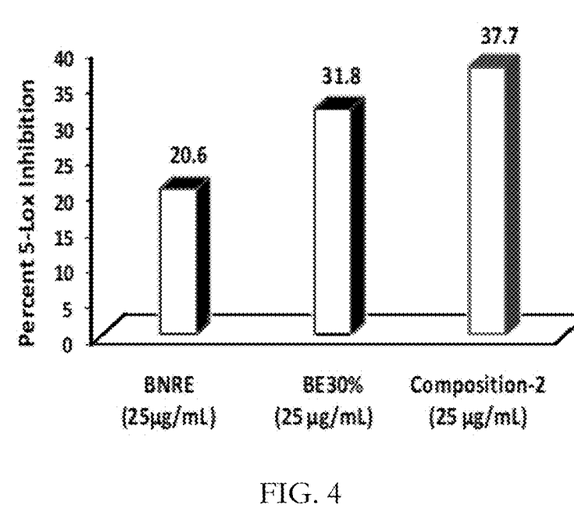
FIG. 4 shows comparative 5-Lipoxygenase inhibitory activity of *Boswellia serrata* extract selectively enriched in 3-O-acetyl-11-keto-β-boswellic acid (AKBA) [BE30%], *Boswellia serrata* non-acidic resin extract (BNRE) and composition-2. The bars represent percentage inhibition of 5-Lipoxygenase enzyme exhibited by BE30%, BNRE and composition-2 at 25 μg/mL concentration.

The said *B. serrata* extracts selectively enriched in AKBA were then combined with a few selected ingredients to obtain compositions having better anti-inflammatory activity. The individual extracts and the compositions were tested for their efficacy to inhibit 5-lipoxygenase enzyme (5-LOX). It was found very surprisingly that a composition comprising *Boswellia serrata* gum resin extract selectively enriched in 30% AKBA (BE30%) and *Boswellia serrata* non-acidic resin extract (BNRE), showed synergistic inhibition of 5-LOX. The composition-2 comprising BE30% and BNRE in 2:1 ratio showed 37.7% inhibition at 25 µg/mL compared to 31.8% and 20.6% inhibitions shown by BE30% and BNRE respectively at the same concentrations. The comparative 5-lipoxygenase inhibition shown by composition-2 and its individual ingredients are presented in FIG. 4.

*Boswellia serrata* extract enriched to 30% AKBA (BE30%), *Boswellia serrata* non-acidic resin extract (BNRE) and Composition-2 were then tested for their efficacy in inhibiting Matrix Metalloproteinase-3 (MMP-3) production in TNFα induced SW982 human synovial cells. The MMP-3 production in cell free culture supernatants was estimated by ELISA development kit (R&D System, Minneapolis, Minn., USA). Surprisingly, the composition-2 exhibited better inhibition of MMP-3 production in synovial cells than those shown individually by both BE30% and BNRE, confirming the synergistic effects shown against 5-LOX. Composition-2, BE30% and BNRE showed 50% inhibitory concentrations ($IC_{50}$) at 46.78, 58.75 and 119.32 µg/mL respectively. The synergistic MMP-3 inhibition shown by composition-2 compared to those shown by its individual ingredients BNRE and BE30% is summarized in FIG. 5.

The synergistic effects shown by composition-2 in vitro were then put to test in vivo in Freund's Complete Adjuvant induced arthritis model of Sprague Dawley rats. The anti-inflammatory efficacies of composition-1 and composition-2, comprising *Boswellia serrata* extract selectively enriched in 3-O-acetyl-11-keto-β-boswellic acid to 30% (BE30%) and *Boswellia serrata* non-acidic resin extract (BNRE) in the ratio 1:1 and 2:1 respectively, were evaluated by an in vivo study in Freund's Complete Adjuvant induced arthritis model of Sprague Dawley rats and compared their efficacy with the efficacy shown by the individual ingredients, BE30% and BNRE. The treatment group rats were supplemented with 100 mg/kg body weight of *Boswellia* extract selectively enriched to 30% AKBA (BE30%) or *Boswellia serrata* non-acidic resin extract (BNRE) or composition-1 or composition-2 for 14 days. The positive control group was supplemented with Prednisolone at 10 mg/kg body weight. At the 14th day, Freund's Complete Adjuvant (FCA) was injected subcutaneously in the sub-plantar region of the left hind paw of each animal. The experiment was terminated on $28^{th}$ day. Blood samples were collected from each animal at regular intervals and paw volumes were measured by Plethysmography equipment on the day of FCA injection and after 13 days of FCA inoculation. The difference in volume of paw edema is considered as the inflammatory response. The in vivo anti-inflammatory responses of BE30%, BNRE, composition-1, composition-2 and prednisolone were estimated by calculating the percentage of inhibition of paw edema when compared to the CMC supplemented control.

The treatment groups supplemented with *Boswellia serrata* extract 30% AKBA (BE30%) and *Boswellia serrata* non-acidic resin extract (BNRE) showed 37% and 10% reduction in paw edema respectively. However, the treatment groups supplemented with composition-1 and composition-2 at the same dose level showed better reduction in paw edema and achieved 44% and 54% reductions in paw volumes respectively. The positive control group supplemented with prednisolone exhibited 53% inhibition at 10 mg/kg dose level. The results as summarized in FIG. 6 confirm the synergistic effects observed in vitro for the inventive compositions-1 & -2.

Figure 7A:
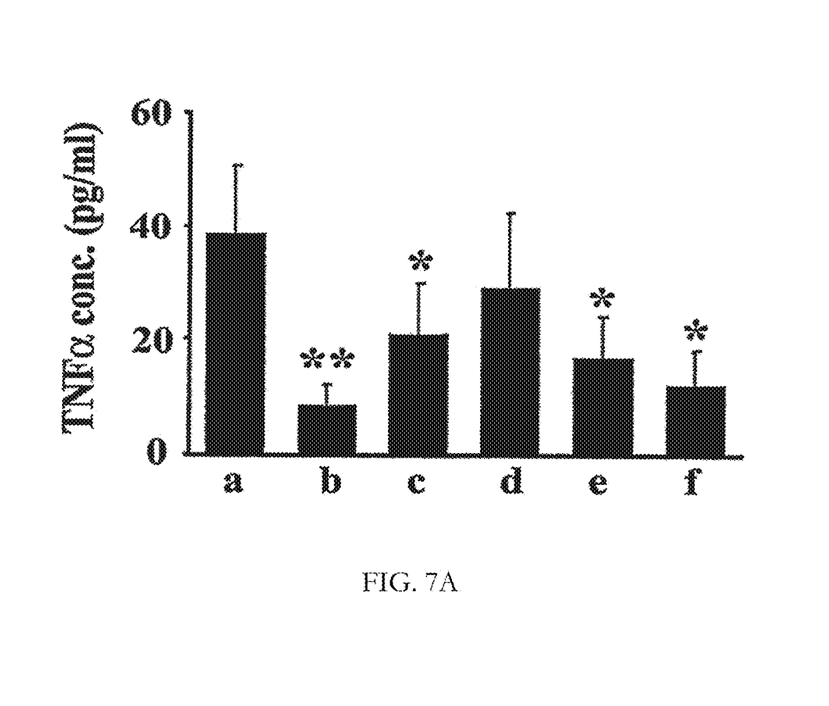
FIGS. 7A and 7B show bar diagrammatic representations of serum TNFα (FIG. 7A) and IL-1β (FIG. 7B) concentrations in different groups of animals. After 14 days of FCA challenge, serum TNFα and IL-1β were quantitatively measured by enzyme-immuno assay kit (R&D Systems, USA). The bars a to f represent the levels of the cytokines in groups supplemented with control, prednisolone (10 mg/kg), BE30% (100 mg/kg), BNRE (100 mg/kg), composition-1 (100 mg/kg) and composition-2 (100 mg/kg), respectively. Each bar represents mean±SD. N=6, * $P<0.05$ and ** $P<0.005$ (vs. control).
Figure 7B:
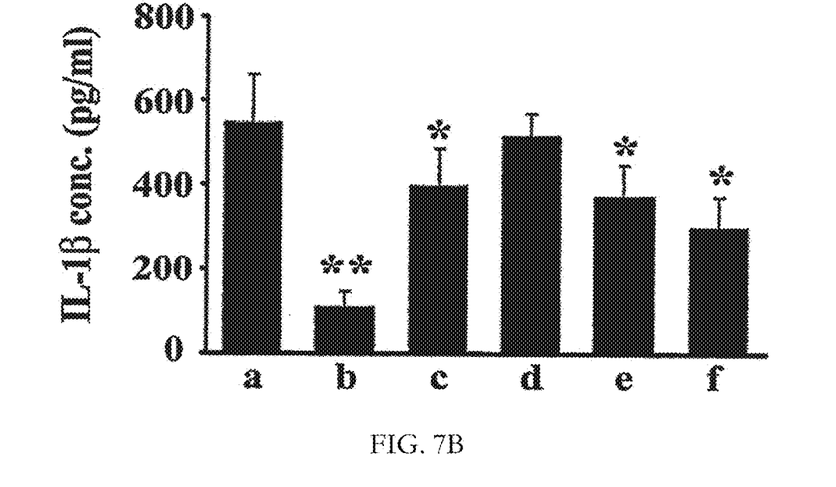

Further, the levels of biomarkers, tumor necrosis factor-alpha (TNF-α) and Interleukin-1beta, (IL-1β) in the serum of the treatment groups and the control group were evaluated. The treatment groups supplemented with composition-1 and composition-2 showed significantly better reduction in the serum biomarkers, TNF-α and IL-1β compared to the levels exhibited by the treatment groups supplemented with the individual ingredients BE30% and BNRE as shown in FIGS. 7A and 7B.

Therefore, the foregoing data shows that compositions comprising AKBA enriched *Boswellia* extract and *Boswellia serrata* non-acidic resin extract (BNRE) are more potent as anti-inflammatory agents compared to the efficacy obtained with the individual components at the same dose level, manifesting an unexpected synergistic association between these extracts.

*Boswellia serrata* extract selectively enriched to contain 30% 3-O-acetyl-11-keto-β-boswellic acid (AKBA) is used to demonstrate the present invention. However any other *Boswellia serrata* extract selectively enriched in the AKBA content from 10% to 100% by weight can also be used for making synergistic composition(s) in combination with *Boswellia serrata* non-acidic resin extract (BNRE).

*Boswellia serrata* extract enriched in the AKBA content from 10% to 100% can be obtained using one or more of the following processes, which include but not limited to (1) conversion of other β-boswellic acids in the commercial *Boswellia serrata* extract to 35-45% AKBA extract using the earlier processes reported by the inventors through their PCT application # PCT/IN05/000074, dated 7 Mar. 2005 and PCT Patent publication WO03074063A1 and granted Indian patent #205269, (2) followed by diluting the conversion product to 10-45% AKBA extract using pharmaceutically or dietically acceptable carrier or diluent or (3) Purification of the above conversion product to 90-99% AKBA using a combination of the steps which include but not limited to column chromatography, partitions, crystallization and the like and then diluting the pure AKBA to desired AKBA concentration (20-99%) using pharmaceutically or dietically acceptable carrier or diluent or low grade commercial *Boswellia serrata* extract (4) alternately, purification of the naturally existing AKBA in the gum resin to a desired concentration in the range of 10-99% AKBA, using a combination of the steps which include but not limited to extraction, column chromatography, partitions, crystallization and the like, and then diluting the higher percentage fraction to desired concentration using pharmaceutically or dietically acceptable carrier or diluent or low grade commercial *Boswellia serrata* extract.

Different embodiments of the present invention are as outlined below:

In one aspect the present invention provides synergistic anti-inflammatory compositions comprising *Boswellia* extract selectively enriched in 3-O-acetyl-11-keto-β-boswellic acid (AKBA) and *Boswellia serrata* non-acidic resin extract (BNRE). The compositions can be used to prevent or cure or treat inflammation and/or one or more disease conditions related to or associated with inflammation.

In another aspect of the invention it was found that there was a synergistic antiinflammatory effect when therapeutically effective quantities of *Boswellia serrata* extract selectively enriched in AKBA and *Boswellia serrata* non-acidic resin extract (BNRE) were combined at certain specific ratio and the effect is better than that obtained when the components were given individually and also there was a synergistic amelioration of the expression or production of pro-inflammatory biomolecules/protein markers.

In a further aspect, the invention provides synergistic compositions comprising *Boswellia serrata* extracts selectively enriched in AKBA extract and *Boswellia serrata* non-acidic resin extract (BNRE) for the amelioration of the expression or production of the biomolecules/biomarkers/ certain redox-sensitive pro-inflammatory genes related to or associated with inflammation which include but not limited to 5-lipoxygenase (5-LOX), 5-Lipoxygenase activating protein (FLAP), macrophage/adipocyte fatty acid-binding protein (aP2/FABP), IFN-γ, IL-4, ICAM, VCAM, Matrix metalloproteinases (MMPs) such MMP-3 and MMP-1, NFκB TNF-α and IL-1β in mammals in need thereof.

In yet another aspect, the invention provides synergistic compositions comprising *Boswellia serrata* extracts selectively enriched in AKBA and *Boswellia serrata* non-acidic resin extract (BNRE) for the prevention, control and treatment of one or more disease conditions related to associated with inflammation which include but not limited to asthma, atherosclerosis, endothelial dysfunction, allergic rhinitis, dermatitis, psoriasis, cystic fibrosis, inflammatory bowel diseases, interstitial cystitis, migraines, angina, chronic prostatitis, sun burn, periodontal disease, multiple sclerosis, uveitis, post-angioplasty restenosis, glomerulonephritis, gastrointestinal allergies, nephritis, conjunctivitis, chronic obstructive pulmonary disease, occupational asthma, eczema, bronchitis, hay fever, hives, allergic disorders and for conditions like wheezing, dyspnea, non productive cough, chest tightness, neck muscle tightness, rapid heart rate, chest pain, joint pain, collagen degradation by UV irradiation, skin-wrinkling and skin-aging and several other conditions associated thereof in mammals.

In still yet another aspect, the invention further provides synergistic compositions comprising *Boswellia serrata* extracts selectively enriched in AKBA extract and *Boswellia serrata* non-acidic resin extract (BNRE) for the prevention, control and treatment of one or more components of inflammation, arthritis, cognition, neurological disorders, Alzheimer's disease, collagen degradation, aging of skin, cholesterol lowering, metabolic disorders and cancer. Non-limiting EXAMPLEs of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, joint disorders, spondyloarthropaties (ankylosing spondylitis), osteoarthritis, hyperuricemia and arthritis associated with acute gout, chronic gout and systemic lupus erythematosus, and degenerative arthritis.

In other preferred embodiment, the invention' further provides a process for producing the *Boswellia serrata* non-acidic resin extract (BNRE), which include extraction of the gum resin of *Boswellia serrata* with a water immiscible organic solvent followed by washing the organic solvent extract with an aqueous alkali solution such as aqueous potassium hydroxide, followed by water and brine, and then finally evaporating the organic layer under vacuum followed by removing the volatile compounds under high vacuum and temperature to obtain BNRE. The water immiscible organic solvent can be selected from hexane, chloroform, dichloromethane, ethyl acetate, methyl isobutyl ketone or any other water immiscible solvent or mixtures thereof.

In a further embodiment, the *Boswellia serrata* intact oil can also be used in place of BNRE for making the synergistic compositions.

In other preferred embodiment, the invention further provides the process for producing compositions comprising the steps including:
(a) extraction of the gum resin of *Boswellia serrata* with a water immiscible organic solvent, filtering the extract carefully to remove the undissolved resin material and then washing the organic solvent extract repeatedly with an aqueous alkali solution such as aqueous potassium hydroxide followed by water and brine, and then finally evaporating the organic layer under vacuum and elevated temperature to remove the solvent, followed by removing the volatile compounds from the oily residue under high vacuum and temperature. to obtain the *Boswellia serrata* non-acidic resin extract (BNRE),
(b) selectively enriching acidic extract of the *Boswellia serrata* gum resin to obtain *Boswellia serrata* extract selectively enriched to 10-100% AKBA (BE),
(c) combining the *Boswellia serrata* non-acidic resin extract (BNRE) and AKBA enriched *Boswellia serrata* extract at desired ratio(s) to obtain present inventive composition(s).
(d) optionally mixing the compositions with one or more ingredients selected from biologically or pharmaceutically acceptable excipients, diluents and additives.

The water immiscible organic solvent in the above process can be selected from hexane, chloroform, dichloromethane, ethyl acetate, methylisobutylketone, tert-butanol or any other water immiscible solvent.

The acidic extract of the *Boswellia serrata* gum resin needed for the enrichment of AKBA can be prepared from the gum resin using a known procedure or selected from a group of commercially available *Boswellia serrata* extracts standardized to boswellic acids, preferably an extract standardized to around 85% total acids by titrimetric method of analysis.

In other embodiment, the invention further provides the method of identifying *Boswellia serrata* non-acidic resin extract (BNRE), which comprises the steps of:
a) Identifying the prominent compounds of BNRE as markers and isolating the same to >98% purity, followed by characterising them thoroughly using spectral data;
b) Injecting a known amount each of the marker compounds individually on to a Phenomenex Luna Phenyl-Hexyl analytical column (4.6×250 mm, 5μ), mounted on to an HPLC system with PDA detector, wherein the column is maintained at 30° C. and eluted with a binary solvent mixture, comprising 0.1% v/v Ortho phosphoric acid in water and acetonitrile at 27% and 73% respectively, at a flow-rate of 1.5 mL/min and measuring the retention time and peak area for each marker using the UV detection at 210 nm and 248 nm; and then, c) Analyzing a known amount of BNRE sample under similar conditions and identifying the markers in the mixture based on a comparison of retention times of the peaks in the sample with those of the standards and optionally by co-injecting the sample along with each of the marker, and then estimating the percentage of each marker in the sample by comparing its peak area with the peak area corresponding to the standard at a known concentration, and then, d) Obtaining the composition of BNRE by expressing the percentages of all the markers together, which include but not limited to nephthenol, serratol, diterpene X, lupeol, olean-12-ene-3β-ol, olean-12-ene-3α-ol, lanosta-8,24-diene-3α-ol, urs-12-ene-3α-ol and guiol, and then using the said composition for comparison with other samples of BNRE.

In yet another aspect of the present invention, the synergistic anti-inflammatory compositions comprising *Boswellia serrata* extracts selectively enriched in AKBA and *Boswellia serrata* non-acidic resin extract (BNRE) contain optionally one or more of pharmaceutically or nutraceutically or dietically acceptable excipient(s) or diluents or salt(s) or additive(s).

The other embodiments of the present invention further provide the usage of the said synergistic compositions as it is or in comminuted form and/or in unmodified form as granules or powder or paste or the active ingredients are formulated into a solid, semi-solid or liquid dosage form by adding a conventional biologically or pharmaceutically acceptable salt(s) or additive(s) or excipient(s).

In a further embodiment, the invention provides that therapeutically effective amount of the novel compositions of the present invention can be administered in a specific dosage form such as orally, topically, transdermally, parenterally or in the form of a kit to a subject or patient in need thereof. Specific dosage form for formulation of the compositions of the present invention includes but not limited to oral agents such as tablets, soft capsules, hard capsules, pills, granules, powders, infusion solution, injection solution, cream, gel, emulsions, ointment, enema, medicinal pack, food supplement, emulsions, suspensions, syrups, pellets, inhalers, mouth sprays and the like; and parenteral agents such as injections, drops, suppositories and the like.

Another embodiment of the invention provides a kit comprising the composition(s) of *Boswellia* extract selectively enriched in 3-O-acetyl-11-keto-β-boswellic acid (AKBA) and *Boswellia serrata* non-acidic resin extract (BNRE). The kit can further comprise instructions for using the composition(s) for control, prevention and treatment of inflammation and inflammatory conditions including but not limited to asthma, arthritis and atherosclerosis.

In a further embodiment of the present invention, the compositions may further comprise effective amounts of one or more pharmaceutical or nutraceutical or dietically acceptable agents including but not limited to antioxidant(s), adaptogen(s), anti-inflammatory agent(s), anti-diabetic agent(s), antiobese agent(s), antiatherosclerotic agent(s), bio-protectants and/or bio-availability enhancer(s) and trace metals or an excipient(s) or pharmaceutically acceptable salt(s) or additive(s) and the compositions or mixtures thereof to form a formulation(s) administered using any of the methods described above.

The EXAMPLEs of pharmaceutically acceptable anti-inflammatory agents employed in the present invention include, but are not limited to prednisolone, hydrocortisone, methotrexate, sulfasalazine, naproxen, diclofenac and ibuprofen.

The EXAMPLEs of the biologically or pharmaceutically acceptable carriers employed in the present invention include, but are not limited to, surfactants, excipients, binders, diluents, disintegrators, lubricants, preservatives, stabilizers, buffers, suspensions and drug delivery systems.

Preferred EXAMPLEs of solid carriers or diluents or excipients include but not limited to glucose, fructose, sucrose, maltose, yellow dextrin, white dextrin, aerosol, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors and preservatives.

Preferred EXAMPLEs of liquid carriers (diluents) include, distilled water, saline, aqueous glucose solution, alcohol (e.g. ethanol), propylene glycol and polyethylene glycol; and oily carriers such as various animal and vegetable oils, white soft paraffin, paraffin and wax.

In alternative aspect of the invention, the inventive compositions of the present invention are delivered in the form of controlled release tablets, using controlled release polymer-based coatings by the techniques including nanotechnology, microencapsulation, colloidal carrier systems and other drug delivery systems known in the art. The said formulation can be designed for once a daily administration or multiple administrations per day.

In accordance to the present invention, the compositions of the present invention can also be formulated into or added to existing or new food and beverage form(s) such as solid foods like cereals, baby food(s), chocolate or nutritional bars, semisolid food like cream or jam, or gel, refreshing beverage, coffee, tea, milk-contained beverage, dairy products, lactic acid bacteria beverage, soup, drop, candy, chewing gum, chocolate, gummy candy, yoghurt, ice cream, pudding, soft adzuki-bean jelly, jelly, cookie, bakery products and the like. These various compositions or preparations or foods and drinks are useful as a healthy food for the treatment and/or prevention of inflammation and/or one or more of disease conditions associated with or related to inflammation including but not limited to asthma, arthritis inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, atherosclerosis, vasculitis, ulcerative colitis, psoriasis, adult respiratory distress syndrome, diabetes, metabolic disorders, delayed-type hypersensitivity in skin disorders and Alzheimer's disease.

Various exemplary embodiments of the invention provides that the amount of present synergistic compositions to be administered or supplemented to humans or mammals may not be uniform and varies depending on the nature of the formulation and suggested human or animal dosage of the extract or the fractions, but preferably, within a range from 0.1 to 750 mg/kg body weight per day, more preferably about 0.5 to 500 mg/kg body weight.

Another embodiment of the invention provides that the quantity of the present inventive compositions in the abovementioned various formulations, food and beverage compositions may also not be uniform and varies depending on the nature of the formulation and suggested human or animal dosage of the compositions, for EXAMPLE, about 0.001% to 99%, more preferably about 0.001 to 90 wt %.

In one of the important embodiments, the concentration of AKBA in the selectively enriched *Boswellia serrata* extract varies in the range of 10% to 100% by weight.

In another embodiment, the concentration of AKBA in the selectively enriched *Boswellia serrata* extract preferably varies in the range of 25%-95% and more preferably 25%-45%.

In yet another embodiment, the synergistic composition can comprise 10%-90% by the weight of *Boswellia serrata* extract selectively enriched in 3-O-acetyl-11-keto-β-boswellic acid (AKBA) and 90%-10% by weight of *Boswellia serrata* non-acidic resin extract (BNRE).

In still another embodiment, the synergistic composition can comprise 30%-70% by the weight of *Boswellia serrata* extract selectively enriched in 3-O-acetyl-11-keto-β-boswellic acid (AKBA) and 70%-30% by weight of *Boswellia serrata* non-acidic resin extract (BNRE).

Another embodiment of the invention is the health care food or beverage comprising any of the ingredients of the above said synergistic compositions up to 0.001% to 80%, preferably 0.001% to 50% by weight based on the total weight of the food or beverage.

Further embodiment of the invention provides that the amount of the present synergistic composition(s) varies in the range of 1% to 100% by weight based on the total weight of the formulation.

In another embodiment, the invention further comprises; mixing the compositions of the present invention with various components used in the animal feed for the purpose of curing, preventing or treating inflammation and several inflammation associated or related diseases including asthma, atherosclerosis and arthritis and the like.

The form of the composition or formulation to be added to animal feed is not specifically limited and may be added it is, or as a composition(s), to various cooked and processed food products. The quantity may be the same as that used in case of food products. Similarly, the ingredients may also be added during or after preparation of the animal feeds.

The following EXAMPLEs, which include preferred embodiments, will serve to illustrate the practice of this invention, and it being understood that the particulars shown are by way of EXAMPLE and for purpose of illustrative discussion of preferred embodiments of the invention and they are not to limit the scope of the invention.

EXAMPLE 1

Preparation of *Boswellia serrata* non-acidic resin extract (BNRE):

The *Boswellia serrata* gum resin (100 g) was dispersed in 600 mL of methyl isobutyl ketone (MIBK) solvent and stirred at room temperature for 60 min. The insoluble gum materials were separated by filtration. The MIBK solution was extracted repeatedly with 2% KOH solution (3×200 mL) to remove the acidic compounds. The MIBK layer was then washed successively with water (400 mL) and brine (200 mL). The MIBK layer was evaporated under reduced pressure at 60-70° C. and the volatile components are removed from the oily residue under vacuum at 75-85° C. to obtain *Boswellia serrata* non-acidic resin extract or BNRE as a viscous oil (12 g).

Alternatively, the gum resin (250 g) collected from *Boswellia serrata* was extracted with methanol (300 mL×3) and the combined methanol extract was concentrated. The residue (50 g) was dissolved in ethyl acetate (400 mL) and extracted thrice with 2N KOH (3×100 mL). The organic layer was washed with water (2×200 mL) and brine (200 mL) and evaporated to obtain *Boswellia* oil. The volatile compounds were evaporated from the oil under vacuum at 75-85° C. to obtain 22 g of *Boswellia serrata* non-acidic resin extract (BNRE).

The BNRE was subjected to column chromatography over normal silica gel. The identical fractions were combined based on TLC and combined fractions were subjected individually to repeated column over silica gel using mixtures of hexane/ethyl acetate or hexane/acetone as eluants to obtain pure compounds. Some of the impure fractions were further subjected to preparative HPLC using a reversed phase C18 silica column to obtain pure compounds. The structures were established by analyzing the $^1$H NMR, $^{13}$C NMR, DEPT, HSQC and HMBC and mass spectral data and then comparing the data with that of known compounds. Nine of the prominent compounds are identified as guiol (1), nephthenol (2), serratol (3), diterpene X (4), lupeol (5), olean-12-ene-3β-ol (6), olean-12-ene-3α-ol (7), lanosta-8, 24-diene-3α-ol (8) and urs-12-ene-3α-ol (9) as depicted in FIG. 1. The pure compounds were then utilized to standardize the *Boswellia serrata* non-acidic extract (BNRE) using HPLC method. The novel composition of BNRE evaluated based on analytical HPLC method and the retention times ($R_t$) is summarized in Table 1 and the HPLC chromatogram was depicted in FIGS. 2A and 2B.

HPLC Method for the analysis of *Boswellia serrata* non-acidic resin extract (BNRE)

TABLE 1

Composition of *Boswellia serrata* non-acidic resin extract (BNRE)

| S. No | Test substance | $R_t$ in min | Percentage |
|---|---|---|---|
| 1 | Guiol (1) | 4.5 | 0.96 |
| 2 | Nephthenol (2) | 7.087 | 2.01 |
| 3 | Serratol (3) | 8.027 | 13.32 |
| 4 | Diterpene X (4) | 15.777 | 0.12 |
| 5 | Lupeol (5) | 26.901 | 0.06 |
| 6 | Olean-12-ene-3β-ol (6) | 31.460 | 1.29 |
| 7 | Olean-12-ene-3α-ol (7) | 33.718 | 5.36 |
| 8 | Lanosta-8,24-diene-3α-ol (8) | 35.371 | 1.34 |
| 9 | Urs-12-ene-3α-ol (9) | 37.207 | 4.55 |

EXAMPLE 2

Method of identification of *Boswellia serrata* non-acidic resin extract (BNRE): The method of identification of BNRE involves the estimation of its composition, which comprises the prominent compounds of BNRE, using the following HPLC method. The solvent gradient is summarized in Table 2. A known amount of each of the marker compounds were analyzed individually, and the retention times and peak areas for each standard compound are noted. A known quantity of BNRE sample was then analyzed under similar conditions and each marker was identified based on a comparison of retention times of the peaks in the sample with those of the standards, and further by co-injecting the sample along with each of the markers. The percentage of each marker in the sample was estimated by comparing its peak area with the peak area corresponding to the standard compound at known concentration as shown below. The composition of BNRE is summarized in Table 3.

HPLC Conditions:
Column: Phenomenex Luna Phenyl-Hexyl, (4.6×250 mm) 5µ,
Wave length: 248 & 210 nm.
Flow rate: 1.50 mL/min
Volume of Injection: 20 µl
Temperature: 30° C.
System: Gradient
Mobile phase: Pump A: 0.1% v/v Ortho phosphoric acid in water
Pump B: Acetonitrile
Wherein, 0.1% v/v Ortho phosphoric acid is prepared by diluting 1 mL of ortho phosphoric acid to 1000 ml with water.

Standards: The prominent compounds of BNRE were selected as markers and isolated the same to >98% purity using a combination of isolation techniques. These pure standards so obtained were thoroughly characterized as guiol (1), nephthenol (2), serratol (3), diterpene X (4), lupeol (5), olean-12-ene-3β-ol (6), olean-12-ene-3α-ol (7), lanosta-8,24-diene-3α-ol (8) and urs-12-ene-3α-ol (9) using a combination of spectral data.

TABLE 2

Gradient Program:

| Time (in min) | Pump-A (%) | Pump-B (%) | Flow rate (ml/min) |
|---|---|---|---|
| 0.01 | 27.0 | 73.0 | 1.50 |
| 40.0 | 27.0 | 73.0 | 1.50 |
| 45.0 | 0.0 | 100.0 | 1.50 |
| 50.0 | 0.0 | 100.0 | 1.50 |
| 52.0 | 27.0 | 73.0 | 1.50 |
| 60.0 | 27.0 | 73.0 | 1.50 |

TABLE 3

Composition of BNRE

| S. No | Name | Retention time (in min) | Wave length (nm) | Composition (%) |
|---|---|---|---|---|
| 1 | Guiol | 4.5 | 210 | 0.96 |
| 2 | Nephthenol | 7.0 | 210 | 2.01 |
| 3 | Serratol | 8.0 | 210 | 13.32 |
| 4 | Diterpine-X | 15.8 | 252 | 0.12 |
| 5 | Lupeol | 26.9 | 210 | 0.06 |
| 6 | Olean-12-ene-3β-ol | 31.6 | 210 | 1.29 |
| 7 | Olean-12-ene-3α-ol | 33.9 | 210 | 5.36 |
| 8 | Lanosta-8,24-diene-3α-ol | 35.5 | 210 | 1.34 |
| 9 | Urs-12-ene-3α-ol | 37.5 | 210 | 4.55 |

Standard Preparation:
Weigh accurately about 10.0 mg of In house reference sample in to a 50 ml volumetric flask, dissolve and make up to volume with Methanol.
Sample Preparation:
Weigh accurately about 250.0 mg of sample into a 50 ml volumetric flask, dissolve and make up to volume with Methanol.
Procedure:
Filter both standard and sample solutions through 0.45µ membrane filter and inject.

Calculation:

$$= \frac{\text{Peak area of sample} \times conc. \text{ of standard} \times \text{purity of } STD}{\text{Peak area of } STD \times conc. \text{ of sample}} = \%$$

EXAMPLE 3

Preparation of *Boswellia serrata* extract enriched to 10-100% AKBA:

Commercially available *Boswellia serrata* extract standardized to 85% total boswellic acids by titrimetric method and comprises 3% 3-O-acetyl-11-keto-β-boswellic acid (AKBA) was used in the process for the selective enrichment of AKBA to 10-100%. The mixture contains total β-boswellic acids [3-O-acetyl-11-keto-β-boswellic acid, β-boswellic acid, 3-O-acetyl-β-boswellic acid, 11-keto-β-boswellic acid, 3-O-acetyl-11-keto-β-boswellic acid] in the range of 45-50% by HPLC method of analysis. The mixture was selectively enriched to contain 35-45% AKBA using one of the procedures described in the PCT application #s PCT/IN02/00034, filed Mar. 5, 2002 and PCT/IN05/000074, filed Mar. 7, 2005. It was further enriched to 45-100% AKBA by adding a chromatography step or crystallization or both to the enrichment process. An enriched extract containing 10-35% 3-O-acetyl-11-keto-β-boswellic acid (AKBA) was prepared by diluting an enriched extract having AKBA in the range of 35-100% with an excipient, preferably white dextrin. The *Boswellia serrata* extract enriched to 30% AKBA (BE30%) is used in the present invention.

EXAMPLE 4

Composition-1: Composition-1 was prepared by mixing unit doses of the following components: One part of *Boswellia serrata* extract enriched to 30% AKBA (BE30%) (1 g) and one part of *Boswellia serrata* non-acidic resin extract (BNRE) (I g).

EXAMPLE 5

Composition-2: Composition-2 was prepared by mixing unit doses of the following components: Two parts of *Boswellia serrata* extract enriched to 30% AKBA (BE30%) (2 g) and one part of *Boswellia serrata* non-acidic resin extract (BNRE) (2 g).

EXAMPLE 6

Composition-3: Composition-3 was prepared by mixing unit doses of the following components: One part of *Boswellia serrata* extract enriched to 30% AKBA (BE30%) (1 g) and two parts of *Boswellia serrata* non-acidic resin extract (BNRE) (2 g).

EXAMPLE 7

Composition-4: Composition-4 was prepared by mixing unit doses of the following components: 3 parts of *Boswellia serrata* extract enriched to 40% AKBA (BE40%) (3 g) and two parts of *Boswellia serrata* non-acidic resin extract (BNRE) (2 g) and one part of white dextrin (1 g).

EXAMPLE 8

Inhibition of 5-LOX and FLAP by *Boswellia serrata* extract enriched to 30% AKBA (BE30%): The effect of BE30% on the key intermediary proteins of arachidonic acid mediated inflammatory pathway was assessed in LPS induced-THP-1 human-monocyte-macrophage cells in vitro. Briefly, THP-1 human monocyte-macrophage cells were pre-treated with 10 µg/ml of BE30% for 1 h and thereafter, the cells were primed with LPS for 2 h to induce the inflammatory response. The cellular proteins were extracted by cell lysis buffer and subjected to immuno-western blot to detect the modulation of expression of 5-Lipoxygenase (5-LOX) and FLAP. BE30% significantly inhibited 5-LOX & FLAP expression in LPS induced-THP-1 human-monocyte-macrophage cells as summarized in FIGS. 3A and 3B.

EXAMPLE 9

5-Lipoxygenase inhibitory activity of *Boswellia* extract 30% AKBA (BE30%), *Boswellia serrata* non-acidic resin extract (BNRE) and Composition-2:

5-Lipoxygenase enzyme inhibitory activity was measured using the method of Schewe et al. (Adv Enzymol, Vol 58, 191-272, 1986), modified by Reddanna et. al., (Methods of Enzymology, Vol 187, 268-277, 1990). The assay mixture contained 80 µM linoleic acid and sufficient amount of potato 5-lipoxygenase in 50 mM phosphate buffer (pH 6.3). The reaction was initiated by the addition of enzyme buffer mix to linoleic acid and the enzyme activity was monitored as the increase in absorbance at 234 nm. The reaction was monitored for 120 sec and the inhibitory potential of the test substances BE30%, BNRE and Composition-2 was measured by incubating various concentrations of test substances two minutes before the addition of linoleic acid. All assays were performed three times. Percentage inhibition was calculated by comparing slope of the curve obtained for test substances with that of the control. The percentage inhibitions of BE30%, BNRE and Composition-1 are summarized in Table 4 and depicted in the FIG. 4.

TABLE 4

5-Lipoxygenase inhibitory activity

| S. No | Test substance | 5-LOX inhibition at 25 µg/mL |
|---|---|---|
| 1 | *Boswellia serrata* extract 30% AKBA (BE30%) | 31.8% |
| 2 | *Boswellia serrata* non-acidic resin extract (BNRE) | 20.6 |
| 3 | Composition-2 | 37.7 |

EXAMPLE 10

Figure 5:
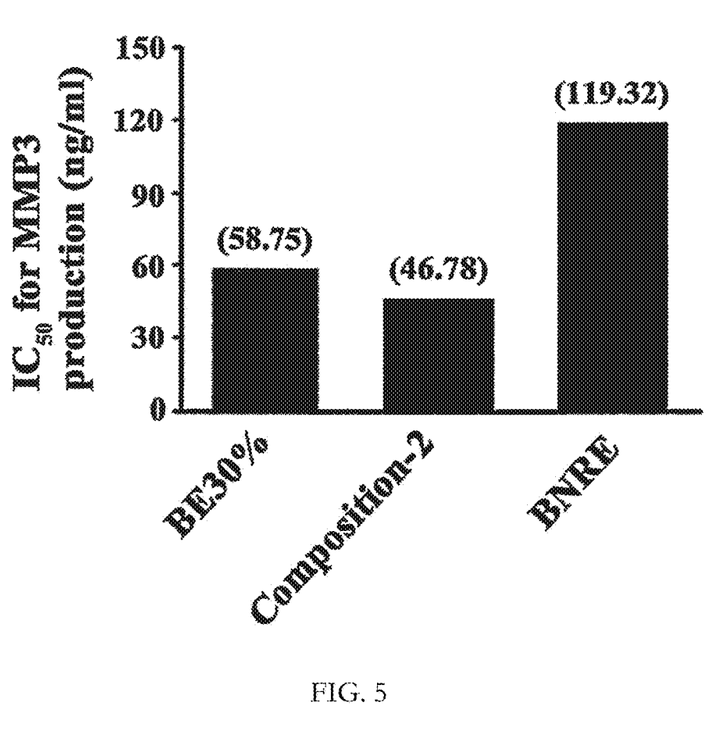
FIG. 5 shows inhibition of Matrix Metalloproteinase-3 (MMP-3) production by *Boswellia serrata* extract selectively enriched in 3-O-acetyl-11-keto-β-boswellic acid (AKBA)[BE30%], *Boswellia serrata* non-acidic resin extract (BNRE) and composition-2. Bars represent 50% inhibitory concentrations ($IC_{50}$) for BE30%, BNRE and Composition-2 in TNFα induced SW982 human synovial cells. The values on the bars represent the corresponding $IC_{50}$ values.

Inhibition of Matrix Metalloproteinase-3 (MMP-) production by *Boswellia serrata* extract 30% AKBA (BE30%), *Boswellia serrata* non-acidic resin extract (BNRE) and Composition-2:

MMP-3 was evaluated in TNFα induced SW982 human synovial cells. Briefly, the SW982 cells were cultured in DMEM with 2 mM Glutamine, 100 U/mL penicillin, 100 mg/mL streptomycin and 10% fetal bovine serum (Hyclone, Logan, Utah). Five thousand cells per well were seeded into a 96-well cell culture plate (Corning, USA) one day before the experiment. The culture media was replaced with fresh DMEM containing 1% fetal bovine serum. *Boswellia* extract 30% AKBA (BE30%), *Boswellia serrata* non-acidic resin extract (BNRE) and Composition-2 were serially diluted in medium, ranging from 5 to 100 ng/ml and were pre-incubated with cells for 2 hour at 5% $CO_2$ at 37° C., and then stimulated with 10 ng/ml human recombinant TNFα (R&D System, Minneapolis, Minn.) for 24 hours. The culture supernatant was harvested and used to measure MMP-3 production by ELISA development kit (R&D System, Minneapolis, Minn., USA). The MMP-3 concentration in cell free culture supernatant was estimated quantitatively by interpolating the optical densities into the standard curve generated from known concentrations of MMP-3. The inhibitory concentration for 50% inhibition ($IC_{50}$) of MMP-3 was calculated from the plot constructed by plotting percentage inhibition against concentration. BE30%, BNRE and Composition-2 showed $IC_{50}$ values of 58.75, 119.32, and 46.78 µg/mL respectively. Their comparative inhibitions are depicted in FIG. 5.

EXAMPLE 11

A synergistic in vivo anti-inflammatory activity of composition-1 and composition-2, comprising *Boswellia* extract selectively enriched in 3-O-acetyl-11-keto-β-boswellic acid (AKBA) to 30%, namely BE30% and *Boswellia serrata* non-acidic resin extract (BNRE), in the ratio 1:1 and 2:1 respectively: The anti-inflammatory efficacies of composition-1 and composition-2, comprising *Boswellia serrata* extract selectively enriched in 3-O-acetyl-11-keto-β-boswellic acid to 30% (5-Loxin) and *Boswellia serrata* non-acidic resin extract (BNRE) in the ratio 1:1 and 2:1 respectively were evaluated by an in vivo study in Freund's Complete Adjuvant induced arthritis model of Sprague Dawley rats. The rats of either sex were randomly selected and divided into five groups containing five animals in each group. The treatment group rats were supplemented with 100 mg/kg body weight of *Boswellia* extract selectively enriched to 30% AKBA (BE30%) or *Boswellia serrata* non-acidic resin extract (BNRE) or composition-1 or composition-2, which contain BE30% and BNRE in 1:1 and 2:1 respectively, for 14 days. The positive control group was supplemented with Prednisolone at 10 mg/kg body weight. All supplements were diluted in 10 mL of 1% CMC for administration. The animals of control group received same volume of 1% CMC. At the 14th day, Freund's Complete Adjuvant (FCA) was injected subcutaneously in the sub-plantar region of the left hind paw of each animal. At the end of experiment, the animals were sacrificed and liver tissue samples were excised and stored in aliquot at −80° C. Blood samples were collected from each animal at a regular interval and paw volumes were measured by Plethysmography equipment on the day of FCA injection and after 13 days of FCA inoculation. The difference in volume of edema at the day of FCA injection and at $13^{th}$ day after induction is considered as the inflammatory response. The in vivo anti-inflammatory responses of BE30%, BNRE, composition-1, composition-2 and Prednisolone were estimated by calculating the percentage of inhibition of paw edema when compared to the CMC supplemented control.

Figure 6:
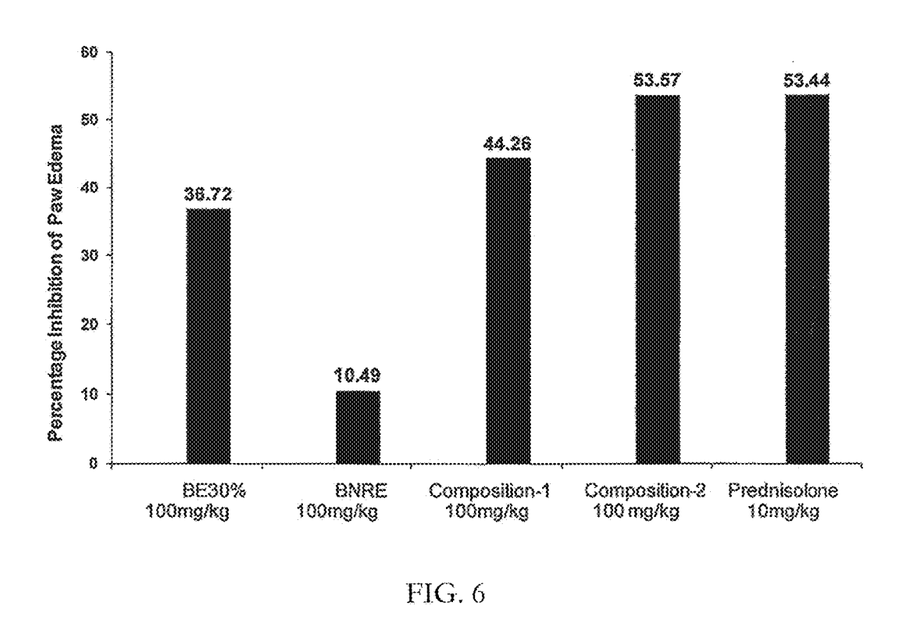
FIG. 6 shows bar diagrammatic representations of percentage inhibition of paw edema volume in Freund's complete adjuvant induced Sprague Dawley rats by *Boswellia serrata* extract selectively enriched in 3-O-acetyl-11-keto-β-boswellic acid to 30% (BE30%, 100 mg/kg) and *Boswellia serrata* non-acidic resin extract (BNRE) (100 mg/kg), Composition-1 (100 mg/kg) and composition-2 (100 mg/kg) comprising BE30% and BNRE in ratio 1:1 and 2:1 respectively, and Prednisolone (10 mg/kg).

The treatment groups supplemented with *Boswellia serrata* extract selectively enriched to 30% AKBA (BE30%) and *Boswellia serrata* non-acidic resin extract (BNRE) achieved 37% and 10% reduction in paw edema respectively compared to 53% inhibition exhibited by the treatment group supplemented with prednisolone as shown in FIG. 6. However, the treatment groups supplemented with composition-1 and composition-2 at the same dose level showed 44% and 54% reductions in paw volumes respectively as shown in FIG. 6. The synergistic efficacy was further substantiated by the evaluation of the biomarkers tumor necrosis factor-alpha (TNF-α) and Interleukin-1beta, (IL- 1β). The treatment groups supplemented with composition-1 and composition-2 showed significantly better reduction in the serum biomarkers, TNF-α and IL-1β, compared to the levels exhibited by the treatment groups supplemented with the individual ingredients BE30% and BNRE as shown in FIG. 7.

It will be appreciated to those of ordinary skill in the art that changes could be made to the embodiments described above without departing from the broad inventive concept thereof. It is understood, therefore, that this invention is not limited to the particular embodiments or EXAMPLEs disclosed, but is intended to cover modifications within the objectives and scope of the present invention as defined by the appended claims.

We claim:

1. An anti-inflammatory composition, comprising a therapeutically effective amount of a combination of:
   from 10% to 90% by weight of the combination of a *Boswellia serrata* extract selectively enriched in 3-O-acetyl-11-keto-β-boswellic acid (AKBA); and
   from 10% to 90% by weight of the combination of a *Boswellia serrata* resin non-acidic, water-immiscible organic solvent extract (BNRE) obtained by selectively removing acidic compounds from a *Boswellia serrata* gum resin extract.

2. The anti-inflammatory composition of claim 1, wherein the *Boswellia serrata* resin non-acidic, water-immiscible organic solvent extract comprises at least three compounds selected from the group consisting of guiol, nephthenol, serratol, diterpene X, lupeol, olean-12-ene-3β-ol, olean-12-ene-3α-ol, lanosta-8,24-diene-3α-ol and urs-12-ene-3α-ol.

3. The anti-inflammatory composition of claim 1, wherein the selectively enriched *Boswellia serrata* extract contains AKBA in a concentration of 10% to 100% by weight.

4. The anti-inflammatory composition of claim 1, wherein the selectively enriched *Boswellia serrata* extract contains AKBA in a concentration of 25% to 95% by weight.

5. The anti-inflammatory composition of claim 1, wherein the selectively enriched *Boswellia serrata* extract contains AKBA in a concentration of 25% to 45% by weight.

6. The anti-inflammatory composition of claim 1, wherein said obtaining the *Boswellia serrata* non-acidic resin extract (BNRE) comprises:
   extraction of gum resin of *Boswellia serrata* with a water immiscible organic solvent,
   filtering the extract to remove undissolved resin material to provide an organic solvent extract;
   washing the organic solvent extract with an aqueous alkali solution to produce an organic layer; and
   evaporating organic solvent from the organic layer to obtain an oily residue; and
   removing volatile compounds from the oily residue under high vacuum and high temperature to obtain the *Boswellia serrata* resin non-acidic, water-immiscible organic solvent (BNRE).

7. The anti-inflammatory composition of claim 1, wherein the composition further comprises at least one excipient, diluent, or additive.

8. The anti-inflammatory composition of claim 7, wherein the at least one excipient, diluent, or additive is selected from the group consisting of distilled water; saline; aqueous glucose solution; ethanol; propylene glycol; polyethylene glycol; an oily carrier selected from the group consisting of animal and vegetable oils, white soft paraffin, paraffin, and wax; glucose; fructose; sucrose; maltose; dextrin; microcrystalline cellulose; calcium stearate; magnesium stearate; sorbitol; stevioside; corn syrup; lactose; citric acid; tartaric acid; malic acid; succinic acid; lactic acid; L-ascorbic acid; dl-alpha-tocopherol; glycerin; glycerin fatty ester; poly glycerin fatty ester; sucrose fatty ester; sorbitan fatty ester; propylene glycol fatty ester; acacia; carrageenan; casein; gelatin; pectin; agar; nicotinamide; calcium pantothenate; amino acids; calcium salts; pigments; flavors; preservatives; and a mixture thereof.

9. The anti-inflammatory composition of claim 1, further comprising at least one pharmacologically acceptable antioxidant, adaptogen, anti-inflammatory agent, anti-diabetic agent, anti-obese agent, or anti-atherosclerotic agent.

10. A dosage form for oral administration, comprising the anti-inflammatory composition of claim 1, wherein the dosage form is a tablet, a capsule, a pill, granules, a powder, an emulsion, a suspension, a syrup, a pellet, or a dietary supplement.

11. A dosage form for transdermal administration, comprising the anti-inflammatory composition of claim 1, wherein the dosage form is a transdermal patch, a cream, a gel, or an ointment.

12. A dosage form for parenteral administration, comprising the anti-inflammatory composition of claim 1, wherein the dosage form is an infusion solution, an injection solution, an enema, drops, or a suppository.

13. A dosage form comprising the anti-inflammatory composition of claim 1, wherein the dosage form is adapted for administration by inhalation.

14. A method for treating inflammation, comprising:
   administering to a subject in need thereof a therapeutically effective amount of the composition of claim 1, optionally in combination with at least one of:
   an excipient, diluent, or additive; and
   a pharmacologically acceptable antioxidant, adaptogen, anti-inflammatory agent, anti-diabetic agent, anti-obese agent, or anti-atherosclerotic agent.

* * * * *